US009907576B2

United States Patent
Mahajan et al.

(10) Patent No.: US 9,907,576 B2
(45) Date of Patent: Mar. 6, 2018

(54) REDUCED SHOCK BREAKAWAY SET SCREW FOR USE WITH A SURGICAL CONSTRUCT

(71) Applicant: The University of Akron, Akron, OH (US)

(72) Inventors: Ajay Mahajan, North Canton, OH (US); Jason King, North Canton, OH (US)

(73) Assignee: The University of Akron, Akron, OH (US)

( * ) Notice: Subject to any disclaimer, the term of this patent is extended or adjusted under 35 U.S.C. 154(b) by 100 days.

(21) Appl. No.: 14/349,708

(22) PCT Filed: Oct. 4, 2012

(86) PCT No.: PCT/US2012/058696
§ 371 (c)(1),
(2) Date: Apr. 4, 2014

(87) PCT Pub. No.: WO2013/052626
PCT Pub. Date: Apr. 11, 2013

(65) Prior Publication Data
US 2014/0236237 A1   Aug. 21, 2014

Related U.S. Application Data

(60) Provisional application No. 61/543,405, filed on Oct. 5, 2011.

(51) Int. Cl.
*A61B 17/70* (2006.01)
*A61B 17/86* (2006.01)
*A61B 90/00* (2016.01)

(52) U.S. Cl.
CPC ........ *A61B 17/7032* (2013.01); *A61B 17/863* (2013.01); *A61B 17/866* (2013.01); *A61B 17/864* (2013.01); *A61B 2090/037* (2016.02)

(58) Field of Classification Search
CPC .......... A61B 17/86–17/8695; A61B 2019/301; A61B 2019/307; A61B 2090/037; F16B 31/021
(Continued)

(56) References Cited

U.S. PATENT DOCUMENTS 1,926,925 A * 9/1933 Wescott .............. E21B 17/0426
                                                           285/115
2,830,635 A    4/1958 Thorstens
(Continued)

FOREIGN PATENT DOCUMENTS

GB           2291156 A       1/1996

OTHER PUBLICATIONS

Khan, et al. "Deformation induced anisotropic responses of Ti-6AI-4V alloy Part II: A strain rate and temperature dependent anisotropic yield criterion" Int. J. Plasticity, pp. 1-13 (2012).
(Continued)

*Primary Examiner* — Jacqueline Johanas
(74) *Attorney, Agent, or Firm* — Renner Kenner Greive Bobak Taylor & Weber

(57) ABSTRACT

A reduced shock breakaway set screw for use with medical implants and constructs for the spine having improved geometry of the groove area between the upper head portion and lower threaded portion of the set screw. The groove area of the set screw has circular and noncircular portions which in at least one embodiment comprise upper and lower radii separated by a flattened groove bottom. Other embodiments have apertures running between the groove area and an internal cylindrical bore and/or ridges or ribs running across the groove area. The improved geometry serves to slow down the fracturing process during shearing thereby increasing the proportion of energy dissipated as heat from plastic deformation of the material to the amount of energy released
(Continued)

as kinetic energy from elastic deformation, thus reducing shock to the patient and physician without changing the preset break-off torque for the set screw.

12 Claims, 10 Drawing Sheets

(58) Field of Classification Search
USPC .......................................... 411/1–4, 393, 419
See application file for complete search history.

(56) References Cited

U.S. PATENT DOCUMENTS

| | | | |
|---|---|---|---|
| 4,076,436 A * | 2/1978 | Slator .................... | E21B 17/04 285/333 |
| 4,338,054 A * | 7/1982 | Dahl .................... | F16B 35/041 29/407.02 |
| 4,492,500 A * | 1/1985 | Ewing ............................. | 411/5 |
| 4,887,596 A | 12/1989 | Sherman | |
| 5,002,542 A | 3/1991 | Frigg | |
| 5,358,285 A * | 10/1994 | Wilson .................... | E21B 17/04 285/114 |
| 5,697,929 A * | 12/1997 | Mellinger .................... | 606/270 |
| 6,004,349 A * | 12/1999 | Jackson ........................ | 606/270 |
| 6,059,786 A * | 5/2000 | Jackson ........................ | 606/916 |
| 6,179,841 B1 * | 1/2001 | Jackson ........................ | 606/301 |
| 6,193,719 B1 * | 2/2001 | Gournay et al. ............. | 606/278 |
| 6,620,167 B2 | 9/2003 | Deslauriers et al. | |
| 6,663,635 B2 | 12/2003 | Frigg et al. | |
| 6,730,089 B2 * | 5/2004 | Jackson ........................ | 606/270 |
| 6,774,870 B2 * | 8/2004 | Mead, Jr. ................. | G02B 7/00 248/603 |
| 6,843,791 B2 | 1/2005 | Serhan | |
| 6,869,433 B2 | 3/2005 | Glascott | |
| 6,929,606 B2 | 8/2005 | Ritland | |
| 6,951,538 B2 | 10/2005 | Ritland | |
| 6,997,927 B2 * | 2/2006 | Jackson ........................ | 606/273 |
| 7,017,457 B2 | 3/2006 | Nessbaum et al. | |
| 7,022,122 B2 | 4/2006 | Amrein et al. | |
| 7,174,615 B2 | 2/2007 | Mark et al. | |
| 7,682,377 B2 | 5/2010 | Konieczynski et al. | |
| 7,708,766 B2 | 5/2010 | Anderson et al. | |
| 7,717,942 B2 * | 5/2010 | Schumacher ...... | A61B 17/7037 606/266 |
| 7,867,257 B2 | 1/2011 | Na et al. | |
| 7,909,834 B2 | 3/2011 | Selover | |
| 7,967,821 B2 | 6/2011 | Sicvol et al. | |
| RE42,932 E | 11/2011 | Martin et al. | |
| 8,167,916 B2 | 5/2012 | Saint-Martin | |
| 8,211,151 B2 * | 7/2012 | Schwab et al. ............. | 606/264 |
| 8,231,635 B2 | 7/2012 | Sharifi-Mehr et al. | |
| 8,249,696 B2 | 8/2012 | Fisher et al. | |
| 8,262,662 B2 | 9/2012 | Beardsley et al. | |
| 8,388,659 B1 * | 3/2013 | Lab et al. .................... | 606/265 |
| 8,523,914 B2 * | 9/2013 | Foley et al. ................. | 606/265 |
| 8,579,568 B2 * | 11/2013 | Wenfeng ............... | A47K 13/26 411/57.1 |
| 8,678,323 B2 * | 3/2014 | Barber .................... | B64G 1/641 244/173.1 |
| 8,684,101 B2 * | 4/2014 | Johnson ................. | A62C 37/16 137/68.15 |
| 2002/0072750 A1 | 6/2002 | Jackson | |
| 2002/0140634 A1 * | 10/2002 | Mead ........................ | G02B 7/00 345/8 |
| 2003/0198528 A1 * | 10/2003 | Onishi .................. | F16B 31/021 411/2 |
| 2004/0202521 A1 * | 10/2004 | Bostik ............................. | 411/2 |
| 2005/0267477 A1 * | 12/2005 | Jackson ........................ | 606/72 |
| 2005/0273101 A1 * | 12/2005 | Schumacher ...... | A61B 17/7037 606/306 |
| 2007/0270859 A1 | 11/2007 | Companioni et al. | |
| 2008/0071273 A1 * | 3/2008 | Hawkes ............. | A61B 17/7007 606/279 |
| 2009/0149889 A1 * | 6/2009 | Peterson et al. .............. | 606/305 |
| 2010/0025050 A2 * | 2/2010 | Johnson et al. ................ | 169/19 |
| 2011/0106165 A1 * | 5/2011 | Schwab et al. .............. | 606/264 |
| 2011/0123287 A1 * | 5/2011 | Tedeschi .......................... | 411/2 |
| 2011/0184471 A1 * | 7/2011 | Foley ................. | A61B 17/7032 606/286 |
| 2011/0306984 A1 * | 12/2011 | Sasing ............... | A61B 17/8888 606/104 |
| 2012/0042502 A1 * | 2/2012 | Wenfeng ................ | A47K 13/26 29/525.04 |
| 2012/0095515 A1 * | 4/2012 | Hamilton ............. | A61B 17/864 606/304 |
| 2013/0131737 A1 * | 5/2013 | Cheng et al. .................. | 606/316 |
| 2013/0221163 A1 * | 8/2013 | Barber .................... | B64G 1/641 244/173.1 |
| 2013/0277527 A1 * | 10/2013 | Dinitz ................... | E01F 9/0182 248/548 |
| 2014/0084113 A1 * | 3/2014 | Barber .................... | B64G 1/641 244/173.2 |
| 2014/0330315 A1 * | 11/2014 | Butler ................ | A61B 17/7085 606/278 |

OTHER PUBLICATIONS

Patel, P. "Screw Fixation of Implants to the Spine" University of Birmingham, pp. 1-267 (Jan. 2010).

Wang, et al. "Numerical Simulation and Fracture Test of Structural Steel Notched Tubes Based on Generalized Strength Model" 2010 Third International Conf. on Information and Computing, pp. 52-55 (2010).

DePuy AcroMed. "Surgical Technique: Monarch Spine System", DePuy AcroMed, Inc., pp. 1-28 (2003).

DePuy Spine. "ISOLA Spinal System, 0902-90-015/H", DuPuy Spine, Inc., pp. 1-95 (2006).

DePuy Spine. "Surgical Technique: Expedium Spine System", DuPuy Spine, Inc., pp. 1-37 (2004).

Synthes. "Click'X System: Technical Guide" Synthes, pp. 1-50 (2007).

Medtronic. "CD Horizon Legacy Spinal System" Medtronic Sofamor Danek USA, Inc., pp. 1-4 (2004).

Medtronic. "TSRH-3D Spinal Instrumentation" Medtronic Sofamor Danek USA, Inc., pp. 1-34 (2005).

"Anatomy of a pedicle screw" Orthopedic Network News, vol. 16, No. 4, pp. 10-12 (Oct. 2005).

* cited by examiner

REDUCED SHOCK BREAKAWAY SET SCREW FOR USE WITH A SURGICAL CONSTRUCT

CROSS REFERENCE TO RELATED APPLICATIONS

This application claims the benefit of U.S. provisional patent application Ser. No. 61/543,405 entitled "Implant Structures that Deform at a Designed Torque and Minimize Shock to Patients and Physicians," filed Oct. 5, 2011, and PCT/US2012/058696 entitled "Reduced Shock Breakaway Set Screw for Use with a Surgical Construct" filed Oct. 4, 2012, both of which are incorporated herein by reference in their entirety.

FIELD OF THE INVENTION

The present invention relates to an improved breakaway set screw for use with surgical constructs for the spine having an improved geometry which reduces the shock to the patient and the surgeon during the set screw break off procedure.

BACKGROUND OF THE INVENTION

Spinal surgery using one or more surgical implants to stabilize, manipulate, and/or repair the spine is well known in the art. One type of common spinal surgery involves fusing or stabilizing two or more vertebra by application of a surgical construct to the posterior surfaces of the vertebra by means of pedicle screws.

There is a large market for pedicle screws and there are numerous designs and manufacturers of this type of fusion device. The spine market in the U.S. is $6.8 billion, and 34% of this market (over $2 billion) involves pedicle screw systems. These systems are usually placed bilaterally and the system on each side is typically composed of a minimum of one stabilizing rod, a pedicle screw for each vertebra, and a set screw at each pedicle screw to secure the stabilizing rod. Sometimes, the securing feature at the head of the pedicle screw is a separate connector. Each company has a slightly different design of the components, but generally, all pedicle screw constructs require a set screw to be tightened to a specific torque to ensure a proper connection between the pedicle screw and stabilizing rod, and thus a rigid fixation. It has been found that if the torque applied to the set screw is insufficient, the construct will loose integrity and the stabilizing rod will not be rigidly fixed as required and could slide or rotate. Additionally, an application of too much torque, it has been found, can result in a fracture of the vertebra or a loosening of the bone-implant connection. Too much torque can also severely deform the screw threads causing them to loose strength and to slip when the patient later puts a load on the spine or surgical construct.

Initially, a surgeon using these types of set screws would simply tighten them by hand until the surgeon judged that the proper tightness had been achieved. The problem with this approach was that there was no objective way for the surgeon to determine whether the set screw had been tightened to the required torque and the surgeon could easily apply too little or too much torque. And if there were a problem with the construct either during surgery or later, it was impossible for the surgeon to prove that the proper amount of torque had been applied.

To address these issues, a variety of systems were developed that utilized torque wrenches of various designs. These systems either required the surgeon to read the torque off the instrument during surgery or provided an audible sound and rotational slip when the proper torque had been reached. One problem with these prior art systems was the difficulty involved in reading the torque measurements or hearing and identifying the sound during surgery. In addition, the torque wrenches used in these systems could loose their precision with use and fail to undergo rotational slip at the target torque.

In another prior art system, the problems of the torque wrench based systems were avoided by means of breakaway set screws having a head designed to shear off the threaded body of the set screw once the proper torque has been achieved. While there are a variety of configurations known in the art, breakaway set screws are ordinarily made from a single piece of titanium alloy and have a hexagonal top portion that mates with a tightening device, a lower threaded set screw portion that mates with a threaded bore of a pedicle screw construct to secure a stabilizing rod, and an annular v-shaped notch separating the two portions.

In these prior art systems, the surgeon uses an extended counter torque tool that holds the top of the pedicle screw and stabilizing rod to try to limit or prevent transmission of the rotational torque used to tighten the set screw from being transmitted to the construct as a whole or to the vertebra of the patient. The shaft of the counter torque tool is hollow and sized to receive the shaft of a break off driver. The break off driver is longer than the counter torque tool and slides through the shaft of the counter torque tool to mate with the hexagonal head of the set screw. As set forth above, the hexagonal heads of these breakaway set screws are designed to shear off the threaded body of the set screw once the proper torque has been achieved. The surgeon simply turns the break off tool while keeping the counter torque tool still, until the hexagonal head shears off the threaded body of the set screw at the pre-determined torque. This set screw break off ("SSBO") procedure is repeated for all of the set screws in the construct. The SSBO procedure is performed 6 times for the average spinal implant construct and many more times for larger constructs in patients with severe deformities such as scoliosis.

Unfortunately, each SSBO imparts an immense, if short lived, shock to both the patient and the surgeon due to the energy released during the catastrophic failure of the metal at the V-shaped notch when the hexagonal head separates from the lower threaded set screw portion. Bench top studies of a prior set screw using accelerometers at various points on and around the pedicle screw have recorded a shock of from about 200 g to about 800 g depending upon a variety of human factors, including how the tool was being held by the surgeon. (FIG. 1A-B) This shock creates significant problems for both the patient and the surgeon. It can lead to the pedicle screw breaking through the side of the vertebra or fracturing the vertebra. The shock can also reduce the pull out strength of the pedicle screw in the patient, thus increasing the chance of a later revision surgery being required. These risks are particularly high for patients suffering with osteoporosis. Further, the repeated shock may also cause premature wear and/or injury to the surgeon's hands and significantly increases the chance that the tools could slip in the surgeon's hands causing pain or injury to the patient.

Accordingly, there is a need in the art for a breakoff set screw for use within a spinal surgery construct, wherein the shock to the patient and physician from the SSBO is reduced.

SUMMARY OF THE INVENTION

In general, the present invention relates to an improved break off set screw for use with surgical constructs for the spine having an improved geometry which reduces the shock to the patient and the surgeon during the set screw break off procedure.

In a first aspect, the present invention provides a reduced shock breakaway set screw for use with a surgical construct comprising a threaded lower portion and an upper head portion separated by a substantially annular groove having circular and non-circular geometry.

In another embodiment, the substantially annular groove of the reduced shock breakaway set screw of the first aspect of the present invention further comprises an upper radius, a lower radius, and a substantially flattened portion separating said upper radius and said lower radius.

In another embodiment, the reduced shock breakaway set screw of the first aspect of the present invention includes any of the embodiments described above wherein said reduced shock breakaway set screw is made of metal.

In another embodiment, the reduced shock breakaway set screw of the first aspect of the present invention includes any of the embodiments described above wherein said reduced shock breakaway set screw is made from a metal selected from the group consisting of titanium and stainless steel.

In another embodiment, the reduced shock breakaway set screw of the first aspect of the present invention includes any of the embodiments described above wherein the metal is titanium.

In another embodiment, the reduced shock breakaway set screw of the first aspect of the present invention includes any of the embodiments described above wherein further comprising an internal opening extending from said upper head portion into said threaded lower portion.

In another embodiment, the reduced shock breakaway set screw of the first aspect of the present invention includes any of the embodiments described above further comprising an internal opening extending from said upper head portion to the top of the threaded lower portion.

In another embodiment, the reduced shock breakaway set screw of the first aspect of the present invention includes any of the embodiments described above further comprising a plurality of apertures extending between said internal opening and said substantially annular groove.

In another embodiment, the reduced shock breakaway set screw of the first aspect of the present invention includes any of the embodiments described above further comprising a plurality of ridges running across said substantially annular groove.

In another embodiment, the reduced shock breakaway set screw of the first aspect of the present invention includes any of the embodiments described above further comprising a plurality of ribs running between said upper radius and said lower radius.

In another embodiment, the reduced shock breakaway set screw of the first aspect of the present invention includes any of the embodiments described above wherein said threaded lower portion further comprises a recess sized to mate with a tool for removing screws.

In another embodiment, the reduced shock breakaway set screw of the first aspect of the present invention includes any of the embodiments described above wherein the upper radius is from about $1/64$ inches to about $1/4$ inches and said lower radius is from about $1/64$ inches to about $1/4$ inches.

In another embodiment, the reduced shock breakaway set screw of the first aspect of the present invention includes any of the embodiments described above wherein the substantially flattened portion has a length of from about 0 inches to about $1/8$ inches.

In another embodiment, the reduced shock breakaway set screw of the first aspect of the present invention includes any of the embodiments described above wherein the substantially flattened portion has a length of 0 inches.

In another embodiment, the reduced shock breakaway set screw of the first aspect of the present invention includes any of the embodiments described above wherein the reduced shock set screw may undergo a surface treatment.

In a second aspect, the present invention provides a reduced shock breakaway set screw for use with a surgical construct comprising a threaded lower portion and an upper head portion separated by a substantially annular groove wherein said substantially annular groove is an arc having a radius greater than the groove wall thickness.

In a third aspect, the present invention provides a substantially annular groove for use with a breakaway set screw having improved geometry wherein the amount of energy released from the plastic deformation of the material in the substantially annular groove during set screw break off is increased.

In another embodiment, the substantially annular groove of the third aspect of the present invention further comprises an upper radius, a lower radius, and a substantially flattened portion separating the upper radius and said lower radius.

In another embodiment, the substantially annular groove of the third aspect of the present invention includes any of the embodiments described above wherein the upper radius is from about $1/64$ inches to about $1/4$ inches and the lower radius is from about $1/64$ inches to about $1/4$ inches.

In another embodiment, the substantially annular groove of the third aspect of the present invention includes any of the embodiments described above wherein the substantially flattened portion has a length of from about 0 inches to about $1/8$ inches.

In another embodiment, the substantially annular groove of the third aspect of the present invention includes any of the embodiments described above wherein said substantially annular groove further comprises an internal opening.

In another embodiment, the substantially annular groove of the third aspect of the present invention includes any of the embodiments described above wherein said substantially annular groove further comprises a plurality of apertures extending between said internal opening and said substantially annular groove.

In another embodiment, the substantially annular groove of the third aspect of the present invention includes any of the embodiments described above wherein said substantially annular groove further comprises a plurality of ridges running across said substantially annular groove.

In another embodiment, the substantially annular groove of the third aspect of the present invention includes any of the embodiments described above wherein said substantially annular groove further comprises a plurality of ridges or ribs running between said upper radius and said lower radius.

In another embodiment, the substantially annular groove of the third aspect of the present invention includes any of the embodiments described above wherein the substantially annular groove is a single arc having a radius that is longer than the groove wall thickness.

In another embodiment, the substantially annular groove of the third aspect of the present invention includes any of the embodiments described above wherein said substantially flattened portion has a length of from about 0 inches to about $1/8$ inches.

In another embodiment, the substantially annular groove of the third aspect of the present invention includes any of the embodiments described above wherein the upper radius is about 1/64 inches to about 1/4 inches and said a lower radius is from about 1/64 inches to about 1/4 inches.

In another embodiment, the substantially annular groove of the third aspect of the present invention includes any of the embodiments described above wherein said annular groove does not have a substantially flattened portion (i.e. length equals 0 inches).

In another embodiment, the substantially annular groove of the third aspect of the present invention includes any of the embodiments described above wherein the upper or lower radii is greater than the groove wall thickness.

In another embodiment, the substantially annular groove of the third aspect of the present invention includes any of the embodiments described above wherein the substantially annular groove may undergo a surface treatment.

The present invention also includes a method of reducing shock to the patient and physician created when breaking off the upper portion of a breakaway set screw for use with a surgical construct at a defined torque using a reduced shock breakaway set screw having a threaded lower portion and an upper head portion separated by a substantially annular groove having an upper radius, a lower radius, and a substantially flattened portion, separating the upper radius and the lower radius.

In another aspect, the present invention may include a method of reducing shock to the patient and physician created when breaking off the upper portion of a breakaway set screw for use with a surgical construct having the method steps of: (i) placing the threaded lower end of a reduced shock breakaway set screw according to the present invention designed to break at a pre-defined torque into a threaded bore of a surgical construct sized to receive it; and (ii) tightening the reduced shock breakaway set screw to the pre-defined torque with a torque applying tool until the upper head portion of the reduced shock breakaway set screw shears away from the threaded lower set screw portion of the reduced shock breakaway set screw.

In another aspect, the present invention may include a method of reducing shock created during set screw break off of a breakaway set screw for use with a surgical construct having a threaded lower portion and an upper head portion separated by a substantially annular groove comprising increasing the ratio of energy released from the plastic deformation of the material in the substantially annular groove to the amount of energy released as kinetic energy from the elastic deformation of the material in the substantially annular groove during set screw break off In another aspect, the present invention may include a method of reducing shock to the patient and physician created when breaking off the upper portion of a breakaway set screw for use with a surgical construct by increasing rotational distance traveled by the torque applying tool from the time the pre-defined torque is reached to the time that the upper head portion of the reduced shock breakaway set screw shears completely away from the threaded lower set screw portion of the reduced shock breakaway set screw.

In another aspect, present invention may include a method of increasing the amount of energy released from the plastic deformation of a ductile material in a substantially annular groove of a breakaway set screw during set screw break off using the reduced shock breakaway set screw described herein.

BRIEF DESCRIPTION OF THE DRAWINGS

For a full understanding of the invention reference should be made to the following detailed description and the accompanying drawings, wherein:

FIG. 10A shows example no. L0R2 ("L0R2") which has a simple groove and 0.0002 inch fillet radius, while FIG. 10B shows example no. L3R8 ("L3R8") which has a 0.0003 inch flat at the bottom of the groove with a 0.0008 inch fillet radius. In both, the lower edge is fixed, while a moment about the central axis is applied to the top edge.

DETAILED DESCRIPTION OF THE ILLUSTRATIVE EMBODIMENTS

The present invention is generally directed to a reduced shock breakaway set screw for use with medical implants having improved geometry of the groove area between the upper and lower portions of the set screw. The geometry serves to slow down the fracturing process during shearing, thereby increasing the proportion of energy dissipated as heat from plastic deformation of the material to the amount of energy released as kinetic energy from elastic deformation. The amount of energy released as shock to the patient or the surgeon is determined by the amount of energy released as kinetic energy of vibration as material elastically deformed and then snaps back to its previous condition.

Figure 2:
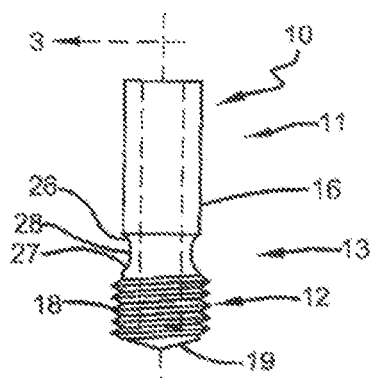
FIG. 2 is a frontal view of a reduced shock breakaway set screw according to one embodiment of the present invention.

Referring now to FIG. 2, a reduced shock breakaway set screw is shown, generally indicated by the numeral 10. The reduced shock breakaway set screw 10 can be made of any ductile metal or other material that may be safely implanted in the human body and will not deform at or about the torque required for shearing. In one or more embodiments, the metal may be selected from titanium alloys, stainless steel and cobalt-chromium alloys. In one embodiment the reduced shock breakaway set screw 10 is made of a commercially available Ti-6Al-4V Titanium alloy. In one embodiment the set screw 10 is made of a commercially available Ti 6Al-4V ELI Titanium alloy. In one embodiment the reduced shock breakaway set screw 10 is made of a commercially available 316L stainless steel. In one embodiment, the reduced shock breakaway set screw 10 may be machined out of a solid piece of a titanium alloy, stainless steel or cobalt-chromium alloy. In accordance with at least one aspect of the present invention, the reduced shock set screw may undergo any of the conventional or otherwise appropriate surface treatments.

The reduced shock breakaway set screw 10 may be adapted to be used in securing a spinal rod or other elongated member within a pedicle screw head, connector, ring, band clamp, bone screw cap, or other portion of a surgical construct in such a way as to substantially eliminate translational or rotational movement of the rod with respect to the vertebra or other parts of the surgical construct. As used herein a surgical construct for use with the spine is a multicomponent device constructed from stainless or titanium-based steel, consisting of solid, grooved, or slotted plates or rods (may be metal or PEEK) that are longitudinally interconnected and anchored to adjacent vertebrae using bolts, hooks, or screws.

Figure 3:
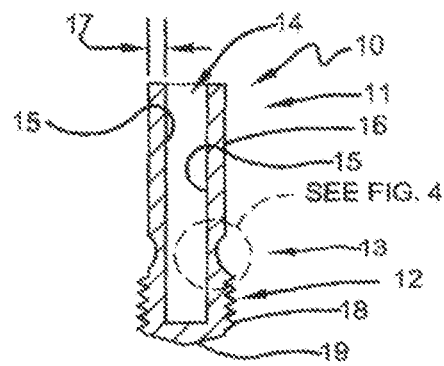
FIG. 3 is a cross sectional view taken along lines 3-3 of FIG. 2 of a reduced shock breakaway set screw according to one embodiment of the present invention.

The reduced shock breakaway set screw 10 has an outer surface 16 and can be divided into an upper head portion 11 and a lower threaded set screw portion 12, separated by a substantially annular groove 13. Referring now to FIG. 3, the reduced shock breakaway set screw 10 may have an internal opening 14 that runs axially down the center of the reduced shock breakaway set screw from the upper head portion 11 to or into lower set screw portion 12. In one embodiment of the present invention the internal opening 14 is machined into the set screw blank as a blind bore running through what will be the upper head portion into what will become the lower threaded set screw portion of the reduced shock breakaway set screw 10. In another embodiment the blind bore stops at the top of what will become the lower threaded set screw portion of the reduced shock breakaway set screw 10. The internal opening 14 is further defined by inner surface 15. The distance between inner surface 15 and outer surface 16 defines a wall thickness 17.

Upper head portion 11 is configured to mate with a torque applying tool (not shown). Upper head portion 11 may be hexagonal in cross section for some or all of its length and sized to fit within and mate with a drive socket of a socket wrench or torque wrench, a manual torqueing instrument, or other torque generating tool having a hollow end portion that is hexagonal in cross section and intimately fits over the upper head portion 11. As will be appreciated by those of skill in the art, upper head portion 11 may have any cross sectional shape so long as it mates with the torque applying tool in such a way as to permit the torque applying tool to apply an amount of torque sufficient to cause the upper head portion 11 to shear off of the threaded lower set screw portion 12. The upper head portion 11 may also have a solid upper portion with a recess shaped to receive within it the end portion of a torque applying tool or a drive bit, so long as the arrangement permits the torque applying tool to apply the necessary amount of torque to cause the upper head portion 11 to shear off of the threaded lower set screw portion 12.

Threaded lower set screw portion 12 has threads 18 and a set screw end 19. The inner surface 15, at the threaded lower set screw portion 12, may contain a set of reverse threads (not shown) to facilitate removal of the set screw with an easy out tool or other screw removal tool after it has been broken off from the upper head portion 11. Alternatively, removal may be facilitated by providing a shaped recess in the top of the lower threaded set screw portion 12 sized to mate with any conventional drive bit or drive end used with a torqueing instrument to impart counter rotations for removal of the set screw portion 12. The threaded lower set screw portion 12 is sized to fit in a threaded bore located in a pedicle screw head, connector, ring, band clamp, bone screw cap, or other similar portion of a surgical construct for use with the spine, to anchor a rod or other elongated member to a pedicle screw.

When reduced shock breakaway set screw 10 is tightened as described above, the set screw end 19 comes into engagement with the rod or other elongated member, holding it in place. The set screw end 19 can be any shape or configuration that can securely hold the rod or other elongated member in place and prevent either translational or rotational movement of the rod or other elongated member. Possible configurations for set screw end 19 may include a v-shaped point coaxial with the set screw portion 12, sharpened ring with or without a v-shaped point coaxial with the set screw portion 12, or any other conventional or otherwise suitable configuration.

Figure 4:
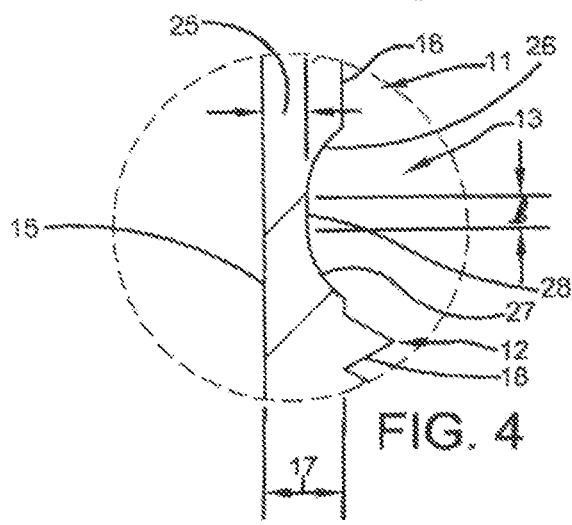
FIG. 4 is a fragmented cross sectional view taken from FIG. 3 of the substantially annular groove of a reduced shock breakaway set screw according to one embodiment of the present invention.

Substantially annular groove 13 runs around the circumference of the reduced shock breakaway set screw 10 between the upper head portion 11 and threaded lower set screw portion 12 of the set screw. In the embodiment shown in FIGS. 2-4, the bottom of the substantially annular groove 13 is elongated, defining an upper radius 26 and a lower radius 27, joined by a substantially flattened portion 28, having a length of l, the substantially flattened portion 28 being tangential to both upper radius 26 and lower radius 27. The substantially flattened portion 28 need not be perfectly flat, but is generally non-circular and not part of either the upper radius 26 or the lower radius 27. The precise dimensions of the upper radius 26, lower radius 27, and substantially flattened portion 28 may depend on the size of the set screw being used. In one aspect of the present invention, the upper radius 26 or the lower radius 27 is greater than the groove wall thickness 25. In one embodiment of the present invention, the upper radius and lower radius may be from 1/64 inches to about 1/4 inches and the substantially flattened portion 28 may have a length l of from more than 0 inches to about 1/8 inches or less.

In an alternative embodiment of the present invention, the substantially annular groove is a single arc having a radius that is longer than the groove wall thickness 25. In this embodiment, there is no substantially flattened portion 28.

Figure 5A:
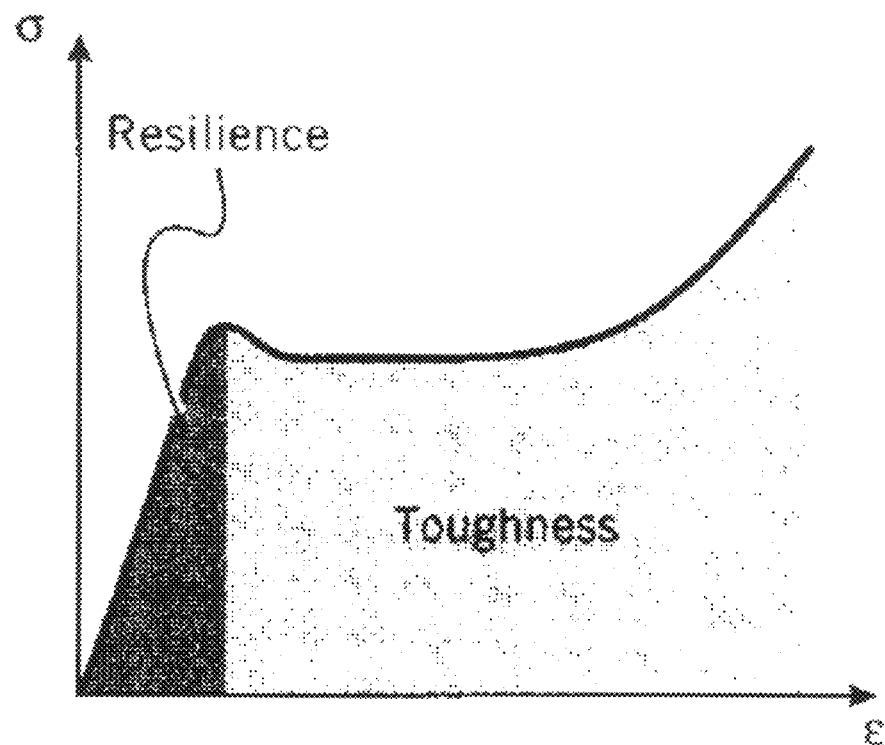
FIG. 5A is a stress strain curve wherein area under the curve is the indicative of a material's toughness.
Figure 5B:
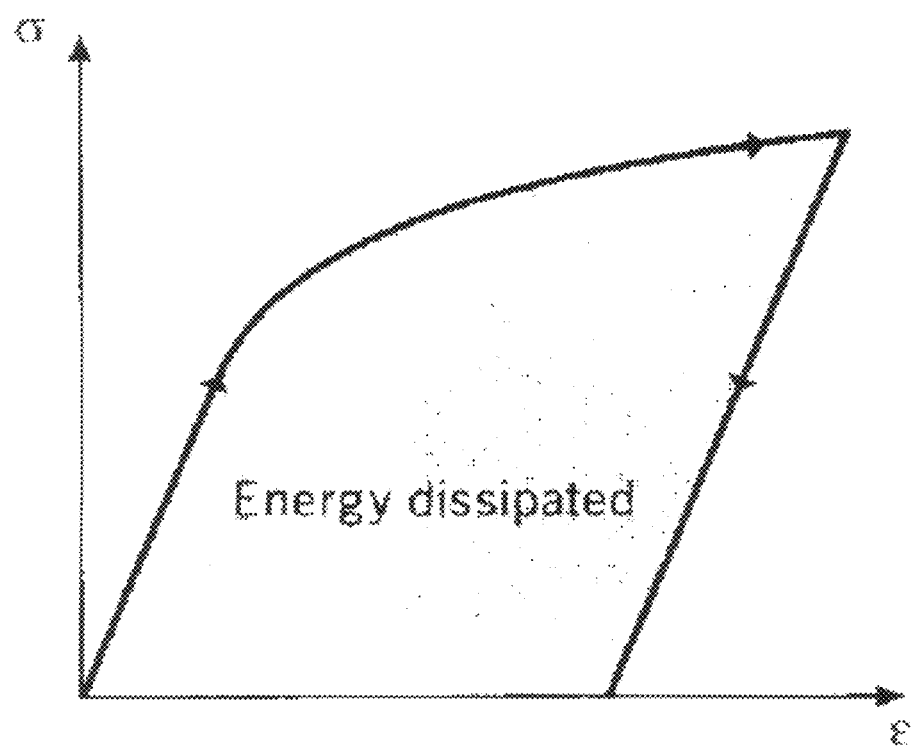
FIG. 5B is a stress strain curve showing energy dissipation.
Figure 14:
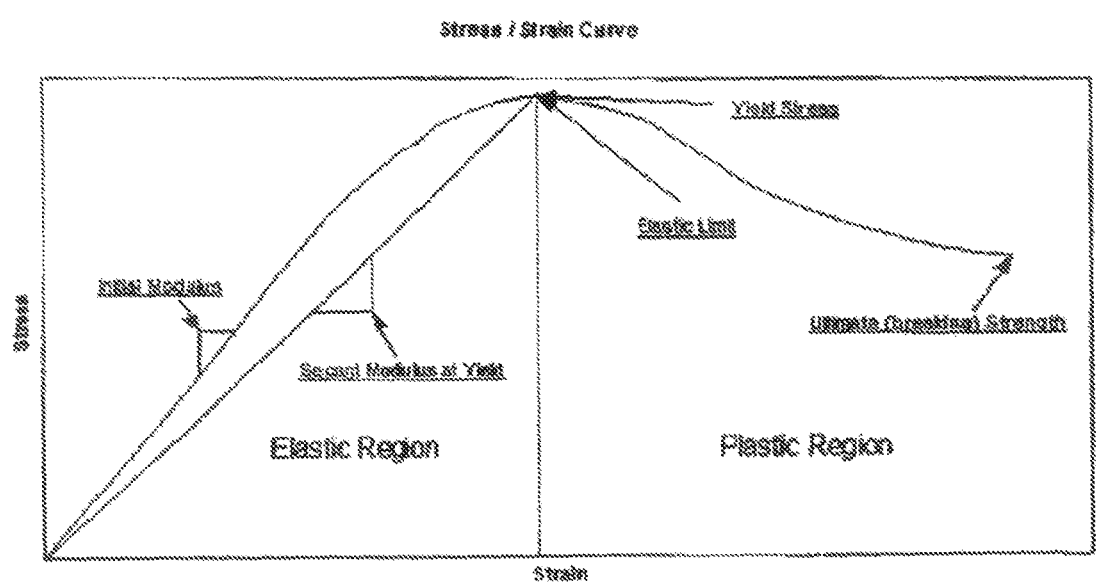
FIG. 14 is a generic stress strain curve showing the elastic and plastic deformation regions.

The external work performed on the device by applying torque to the reduced shock breakaway set screw 10 is primarily converted into either plastic dissipation energy or recoverable elastic strain energy that manifests itself as shock. FIG. 14 is a generic stress strain curve showing areas of elastic and plastic deformation. Plastic deformation for most materials is caused when the structure undergoes so much stress that the bonds between individual atoms break and reform to an adjacent atom. Plastic deformation happens in the direction that these atoms move. Essentially, this concept relies on the material's toughness, or energy absorption potential before failure. Visually, one can see a material's toughness by observing the area under the engineering stress-strain curve (See FIG. 5A). When a metal is elastically deformed, there is no such breaking and reforming of bonds within the metal and if the material breaks/shears under only elastic deformation, the material will snap back to its original shape releasing essentially all of the elastic strain energy as kinetic energy in the form of vibrations (i.e. shock).

Therefore, it is believed that as the elastic strain energy decreases relative to plastic dissipation energy, the shock will also decrease. As would be clear to one of ordinary skill in the art from simple geometry, as the upper head portion of the breakaway set screw undergoes increased rotation before failure, then more elements must be experiencing deformation assuming that the plastic strain limit of each element is identical. As more elements experience deformation, then more energy is dissipated plastically.

The improved groove geometries of the present invention act to increase the proportion of the energy that is released as heat from the plastic deformation of the material in the substantially annular groove, thereby reducing the amount of kinetic energy released from the elastic deformation of the metal in the substantially annular groove, and, accordingly, the shock transmitted to the patient and surgeon.

Given the same pre-set shearing torque for the same material with identical bulk and surface properties, the geometric changes in the substantially annular groove 13 of the set screw 10 can influence the energy release behavior of a crack such that the maximum shock released upon breaking/shearing is reduced. It has been found based on the theory of Linear Elastic Fracture Mechanics (LEFM), that where the stress at the moving crack tip is considered linear elastic with two-dimensional stress, the crack undergoes a rapid, brittle propagation through the structure's thickness when it exceeds a "critical stress intensity." At this critical stress intensity, the energy release rate (G=energy per unit length along the crack tip) of the separating material (potential energy release of the elastic strain) is greater than the crack resistance. The excess of energy becomes kinetic energy which controls the crack tip speed through the material, with the total kinetic energy equal to:

$$E_{kin} = (G-R)da$$

Where:
$E_{kin}$: kinetic energy
G: energy release rate
R: crack resistance force.

Assuming that: (1) the stress during crack propagation is constant; (2) G is independent of crack speed; and (3) R is constant.

Figure 6A:
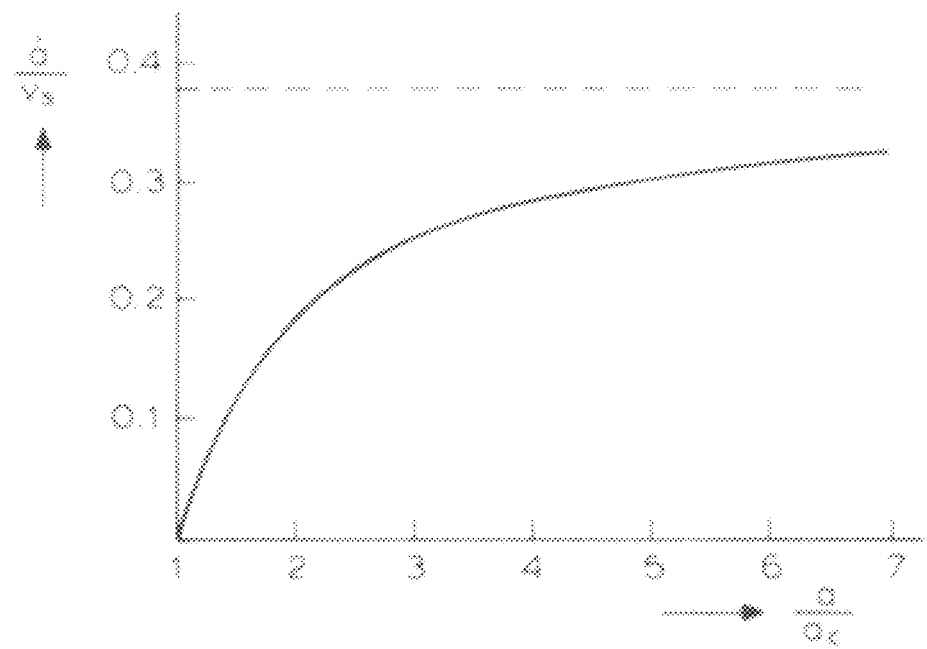
FIG. 6A is a graph showing crack growth rate as a function of crack size.
Figure 6B:
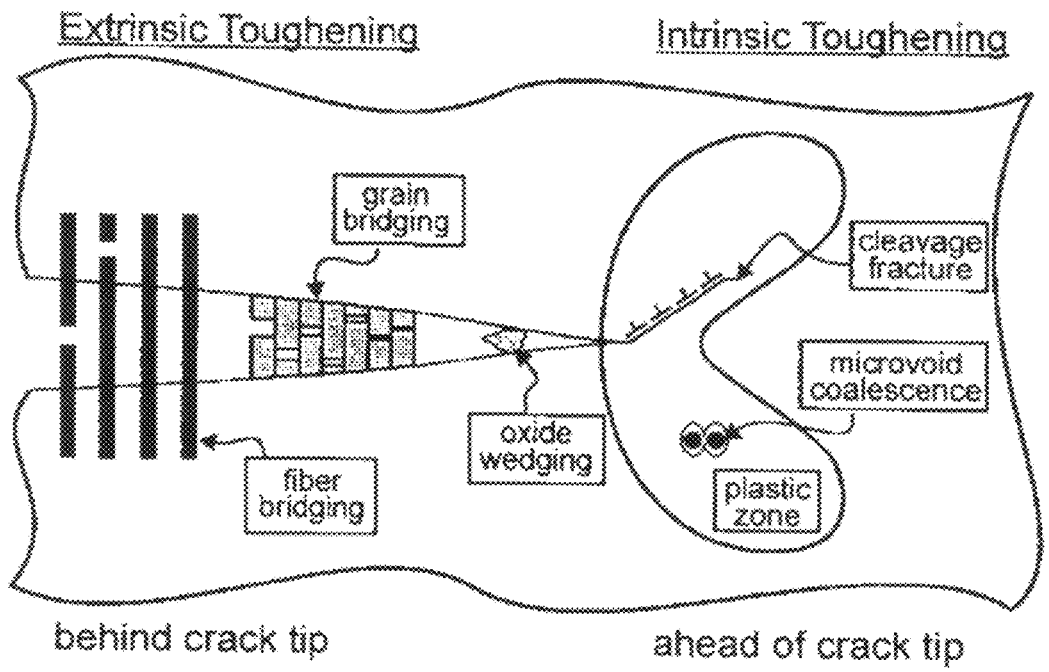
FIG. 6B is an illustration of the competing intrinsic (promoting) and extrinsic (impeding) forces in crack propagation.

Crack resistance and propagation forces are actually a complex combination of a variety of forces, depending on things such as environment, material, and crack/structure geometry. The preceding equation is only a rough guide since, for example, crack resistance does not remain constant, because as crack growth rate is controlled by crack size (FIG. 6A) along with other factors. The primary groupings of these forces that influence crack growth are intrinsic and extrinsic as shown in FIG. 6B. See, Ritchie, R. O., Gilbert, C. J., & McNaney, J. M. (2000). *Mechanics and mechanisms of fatigue damage and crack growth in advanced materials*. International Journal of Solids and Structures. 37:311-329, the disclosure of which is incorporated herein by reference. Intrinsic forces stimulate crack growth and are dependent on the material properties, while the extrinsic forces hinder propagation and are primarily a function of crack size/geometry. Ductile materials such as metals predominantly toughen intrinsically, whereas brittle materials toughen through extrinsic forces. Material and process variabilities such as strain rate, strain hardening, surface irregularities, surface processing (e.g. Shot peening, electro polishing), and grain structure all affect a part's macroscopic behavior through their influence on the microscopic intrinsic and extrinsic properties.

As a general rule, however, it is clear that: (1) the crack propagation rate increases as the crack grows; (2) crack propagation will become brittle when the growth rate is too fast because R is smaller than the energy release rate, resulting in an abundance of kinetic energy (i.e. shock) and (3) metals primarily toughen due to intrinsic crack initiation forces.

The improved groove geometry of the present invention has been found to slow the rate of crack growth thereby dissipating more of the stored energy for plastic deformation and eventually less as shock. By broadening the substantially annular groove 13 and reducing or eliminating the sharp corners or acute angles in the groove 13, the improved groove geometry of the present invention slows the crack propagation by providing increased pathways along the grain boundaries for the crack to propagate, wherein dissipating more energy in plastic deformation, thereby less as shock.

Figure 1A:
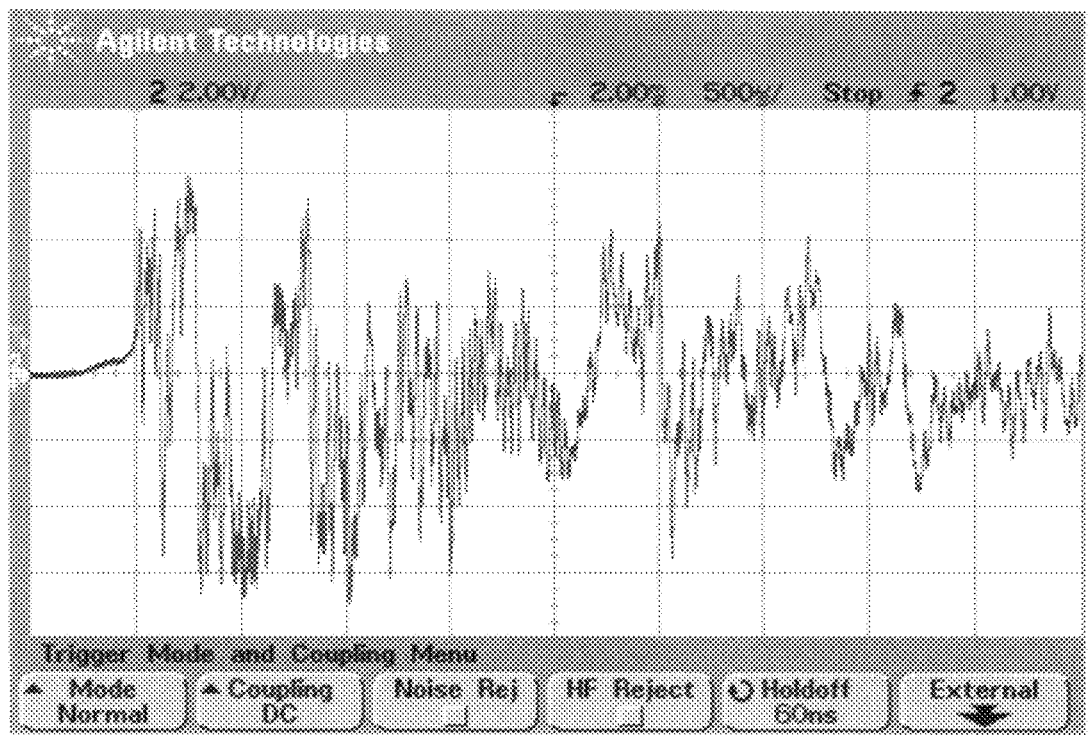
FIG. 1A is a printout of an oscilloscope output of the initial accelerometer signal recorded during SSBO of a commercially available prior art breakaway set screw.
Figure 1B:
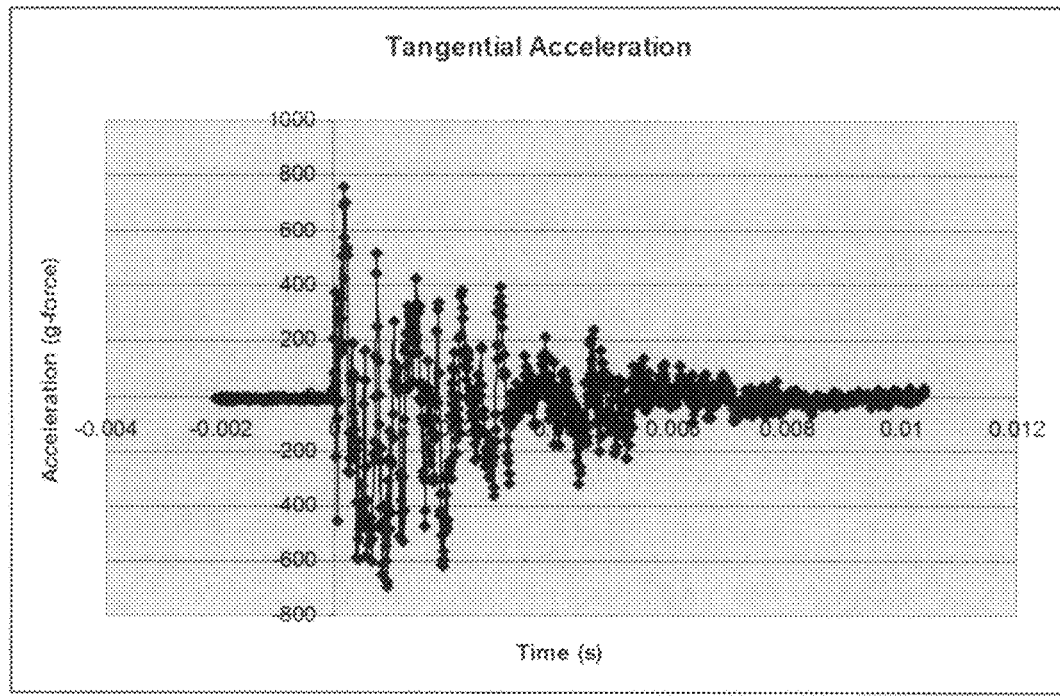
FIG. 1B is a graph of the test data of FIG. 1A wherein the data has been converted to show acceleration (g-forces) per unit time.

By contrast, the prior art SSBO breakaway set screws having a substantially "V" shaped notch with straight angled sides and a very sharply angled bottom, provide a sudden release of energy as a result of the instantaneous shear failure experienced when the surgeon achieves the designed torque. This is illustrated in FIGS. 1A and 1B by the high acceleration peak at the start of the signal, which indicates that crack initiation and propagation is rapid. This SSBO crack speed, together with the set screw geometry, greatly influence the failure behavior of the prior art set screws, and make the normally ductile material response of the metal become primarily a brittle rupture.

Figure 7:
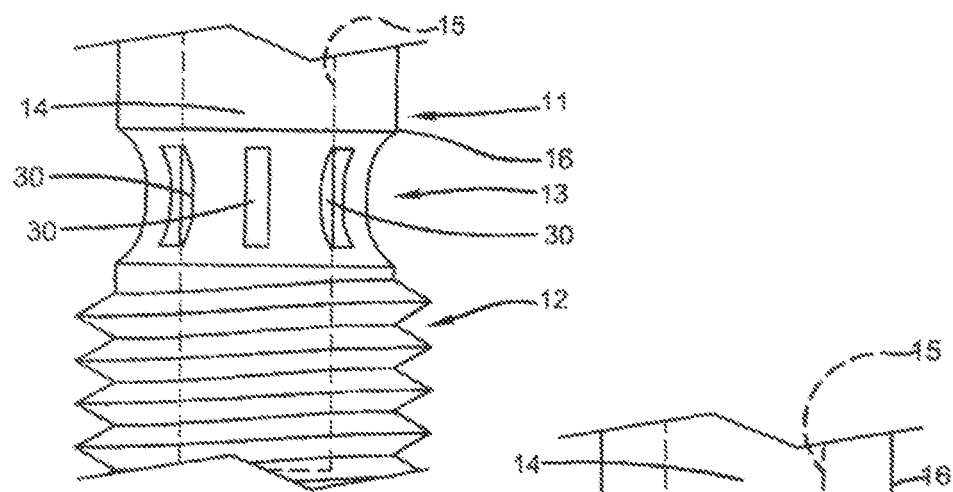
FIG. 7 is a partial frontal view of a reduced shock breakaway set screw according to one embodiment of the present invention having apertures between the substantially annular groove and an internal opening.

In the embodiment best seen in FIG. 7, there are one or more apertures 30 running between the substantially flattened portion 28 and the inner surface 15 of the inner opening 14. These apertures 30 may be evenly spaced along the substantially annular groove 13. In an embodiment best seen in FIG. 8, there are one or more ridges or ribs 29 running from the upper radius to the lower radius of the substantially annular grove 13. Ridges or ribs 29 may be any shape and may be any periodic increase in groove wall thickness 25. These ridges or ribs 29 may be evenly spaced along the substantially annular groove 13. In one embodiment, the ridges or ribs 29 may be contiguous with the substantially flattened portion 28 some or all of the upper and lower radii 26, 27. In one embodiment, there are both a plurality of apertures 30 and a plurality of ribs 29 alternately arranged and evenly spaced along the substantially annular groove 13 as in FIG. 9. In one embodiment, ridges or ribs 29 are variations in the groove wall thickness 25.

The purpose of the apertures 30 is to provide a geometry that initiates crack propagation at multiple points so that there are no an extremely long cracks, since the crack speed is influenced by crack size (FIG. 6B). The multiple holes are intended to increase the amount of energy dissipated through plastic deformation since each crack initiation site must undergo a certain amount of intrinsic toughening. Therefore, in order for the part to fail, complete shear cannot rely on the brittle kinetic energy of one crack spreading circumferentially. At the tip of crack propagation, plastic deformation dissipates energy, and this design causes plastic deformation around the entire circumference since the plastic zone will always be leading the propagating crack. It has been found that tubes with two holes have more ductility before failure than tubes with one hole. The holes are a geometric stress riser that initiates crack propagation. At the intrinsic tip of slow crack propagation, plastic deformation dissipates energy. The multiple holes are intended to increase the amount of energy dissipated through this plastic deformation since each crack initiation site must undergo a certain amount of intrinsic toughening and slow propagation. Therefore, the brittle energy release at the crack tip cannot be the main driver of crack propagation in these geometries, as the critical stress intensity must be reached independently in each section between the holes.

The ridges or ribs 29 are meant to provide added support so that the crack propagation does not initiate until the desired initial torque is reached and further, to delay and guide crack propagation. The ridges or ribs 29 should force additional cracks to require initiation and/or add resistance to reduce crack growth rate thereby reducing kinetic energy release. The ridges or ribs 29 should force additional cracks to require initiation and/or add resistance to reduce crack growth rate, thereby reducing energy release rate. Ideally, this design will cause significant plastic deformation around the entire circumference since the plastic zone will always be leading the slowly propagating crack, while the process will still seem instantaneous to the surgeon because of the greatly reduced length that each crack must travel.

Figure 8:
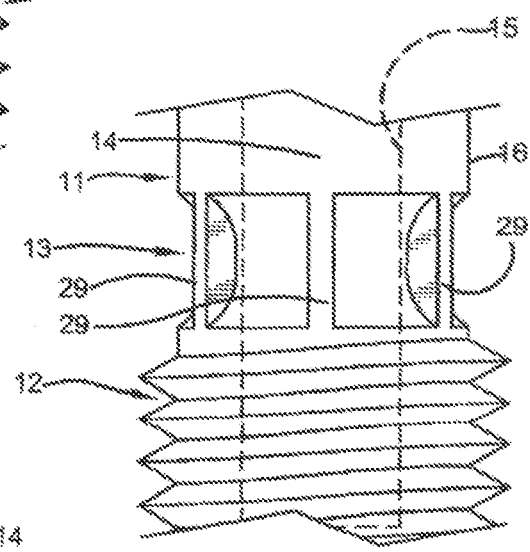
FIG. 8 is a partial frontal view of a reduced shock breakaway set screw according to one embodiment of the present invention having ribs running across the substantially annular groove.
Figure 9:
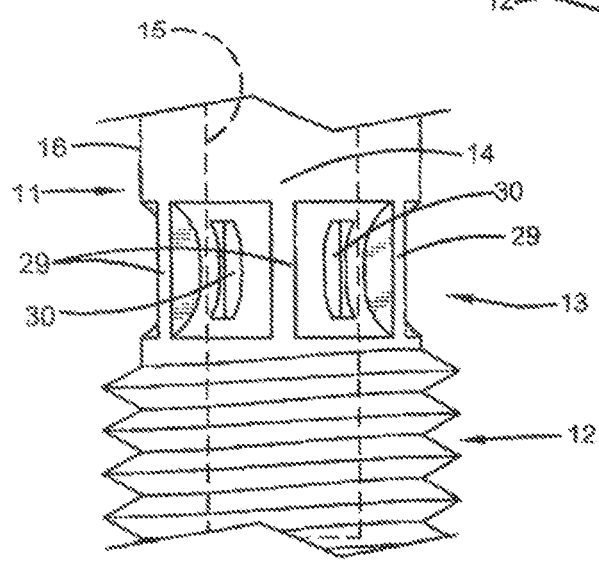
FIG. 9 is a partial frontal view of a reduced shock breakaway set screw according to one embodiment of the present invention having both apertures between the substantially annular groove and an internal opening and ribs running across the substantially annular groove.

The embodiments shown in FIGS. 7-9 may have the same cross sectional area being sheared, and, therefore, result in an identical release of energy compared to the prior art systems. However, this energy release is over a longer period, and may be continuous or occur in observable spikes at intermittent times within the time period of shearing failure. Regardless of the shape of the profile curve, the area under the curve should remain relatively constant if the cross section remains the same since the same energy will be required to shear it.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present.

Example 1

Experimental and Evaluation Validation of Manufacturer Specified Set Screw Break Off (SSBO) Torque for Prior Art Set Screw As set forth above, the proper torque for the set screws is critically important in pedicle screw systems. Not enough torque can allow the stabilizing rod to slip. Over-torque of the set screw can severely deform the screw threads, causing them to lose strength, and possibly allowing the rod to slip when the patient later puts load on the spine. Materials engineering and machine design theories, as well as performing a test using a torque wrench, validated that the prior art set screw tested does break at the torque specified by the manufacturer.

The shear failure during SSBO was explored experimentally and by applying distortion energy theory to thin wall torsion (TWT) and fully plastic torque (FPT) equations. SSBO design torque of 11.00 N-m (as supplied by the manufacturer) was compared to an experimental torque wrench measurement and to the torque required to reach the shear strength calculated by distortion energy theory in both TWT and FPT.

The basic information requirements of TWT and FPT were obtaining the inner diameter (ID) and outer diameter (OD) of the set screw, and calculate the shear strength. First, digital imaging and micrometer readings were used to determine the inner and outer diameters of the set screws at the point of failure (Table 1). Second, From the Distortion Energy (Von Mises) principles:

$$\tau \text{ yield} = \frac{\sigma_{yield}}{\sqrt{3}}$$

Using material data of titanium alloy 6-Aluminum 4-Vanadium (Ti-6AL-4V), which is the primary material from which many implants are made, Quasi-static yield stress for Ti-6Al-4V was determined to be 950 MPa. Therefore, τ yield is about 548 MPa.

TABLE 1

ID and OD measurements of prior art set screw

| | From Digital Image Analysis | Validation from a micrometer |
|---|---|---|
| Inner diameter (ID) | 0.005235 m | 0.0053 m |
| Outer diameter (OD) | 0.0061111 m | 0.0061 m |

In thin wall torsion, the stress in the wall of a tube is assumed to be independent of the radius. Therefore, the standard torsional stress equation is combined with the circular tube polar moment of inertia:

$$\tau = \frac{T*r}{J}$$

$$J = \frac{\pi*(OD^4 - ID^4)}{32}$$

Break-off occurs when there is full plasticity at τ yield, since the stress is considered constant throughout. The mean radius is used:

$$T_{break\text{-}off} = \frac{\tau_{yield} * \pi * (OD^4 - ID^4)}{32 * r_{mean}}$$

This break-off torque is 11.24 N-m.

Fully plastic torque of a hollow shaft is calculated by subtracting what the torque carrying capacity would have been of a rod (of the same material) with a diameter equal to the ID from the torque carry capacity of a solid bar with the diameter equal to the OD:

Ttube=Tsolid−Thollow

The torque of each section, Tsolid and Thollow, is calculated by:

$$T = (\frac{\pi}{12})Ty\ D3$$

Distortion energy is again used for τy. The value of Tsolid is 32.56 N-m, and Thollow is 21.36 N-m. Thus, the FPT break-off torque is:

Ttube=32.56−21.36=11.2 N-m

Finally, a torque wrench (valid from 3.6 N-m to 29 N-m) validated the maximum torque reached before break-off as approximately 11.3 N-m. A comparison of all the failure torques is in Table 2.

TABLE 2

Comparison of Torque Values

| Method | Torque Value (N-m) |
|---|---|
| Design break-off torque (as supplied by Medtronic) | 11.00 N-m |
| Thin Wall Torsion (TWT) | 11.24 N-m |
| Fully Plastic Torque (FPT) | 11.2 N-m |
| Torque wrench | 11.3 N-m |

Example 2

Axisymetric-with-Twist Computer Modeling Experiments

Axisymetric-with-twist computer modeling experiments have been conducted using commercially available modeling software manufactured by Dassault Systèmes Simulia Corp. and sold under the tradename Abaqus (version 6.10-2). These experiments confirmed that geometric manipulations of the groove significantly affects the plastic behavior of the structure while still allowing the maximum torque to be separately controlled.

An explanation of the different components of energy that were tracked for the whole model may be found in the "Energy Balance" section 1.5.5 of the Abaqus Theory Manual, the disclosure of which is incorporated herein by reference. These were referred to by the software as "field variables," with ALLPD referring to the plastically dissipated energy and ALLSE referring to the recoverable elastic strain energy. ALLWK refers to all of the external energy added to the model as it is turned. Another critical variable was rotational strain before failure. The rotation of each test was constant and took exactly one time increment to reach the final rotation location specified (at a constant velocity).

The law of conservation of energy states that energy can neither be created nor destroyed. In addition, since basic material laws state that plastic strain is irreversible deformation of a material, then the amount of plastically dissipated energy accumulated can never be decreased. However, since the Abaqus model being utilized deletes elements when they have surpassed the strain limit defined by the material, the plastically dissipated energy contained in each deleted element is also deleted. Therefore, since every shear model run showed that the geometry sheared all the way through, the point at which fracture completed is also the point at which the last element was deleted and the last decrease in ALLPD was observed.

Modeling decisions were made based on recommendations given in "Classical Metal Plasticity" of the Abaqus 6.10 Analysis User's Manual of the disclosure of which is incorporated herein by reference. The progressive damage and failure models in Abaqus are able to model both quasi-static and dynamic situations. It was determined that the manually applied strain rates in the set screw break off are not high enough to significantly affect the failure stress, thus quasi-static modeling was used. This assumption is due to the Ti 6Al-4V yield strength used in the initial calculations (described above in Example 1), which corresponds to the actual measured and designed for break off torque. This yield strength is the quasi-static yield strength, as higher strain rates result in higher yield strength. The damage model utilized was ductile damage (i.e. failure strain as a function of triaxiality) since the validity of material models can be judged based on their ability to correctly determine the failure strain throughout all loading conditions (as identified by triaxiality values). Therefore, since the damage model used was defined by maximum equivalent strain at a particular triaxiality, equivalent plastic strain (PEEQ) is used to visualize plastic deformation. (Additional information may be found in Abaqus/CAE User's Manual 12.9.3 "Defining Damage" the disclosure of which is hereby incorporated by reference in its entirety.

The method used generally involved creating a 2D axisymmetric sketch of the part, creating a material with damage conditions, assigning the material to the part, creating a mesh on the part using CGAX3 element that allows twist, assigning node regions to which boundary/rotational conditions were applied (FIG. 10), and setting the convergence behavior. The element type utilized, CGAX3, was particularly important to the entire model and simulations because it provided the 2D model an additional degree of freedom. Traditional 2D axisymmetric analysis only allows in-plane movement. Per Abaqus Analysis User's Manual 25.1.6 "Axisymmetric solid element library," the disclosure of which is hereby incorporated by reference in its entirety, the element type CGAX3 also allows elements the freedom to twist about the axis. Movement, moment, and stresses due to torsion on the modeled structure could not have been obtained without this additional degree of freedom. The overall length of the modeled sections remained the same; however the fillet radius and length of the substantially flattened portion of the bottom of the groove was varied. The fillet radii values were 0.0002 in ("R2"), 0.0004 in ("R4"), and 0.0008 in ("R8") with the length of the flattened bottom section ranged from 0.0 in ("L0") (i.e. a simple semicircle groove with no flattened bottom section) to 0.0003 in in increments of 0.0001 in ("L1," "L2," and "L3," respectively). These measurements were only used to determine relative performance in Finite element modeling, and they are not the intended measurements of the invention herein.

Figure 10A:
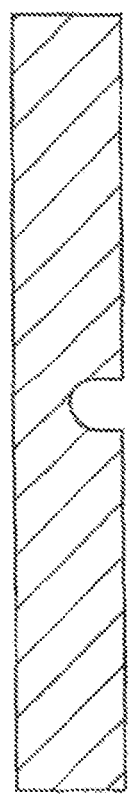
FIGS. 10A and 10B shows the axisymmetric cross sections of the two most dissimilar geometries used for the axisymetric-with-twist computer modeling trials.
Figure 10B:
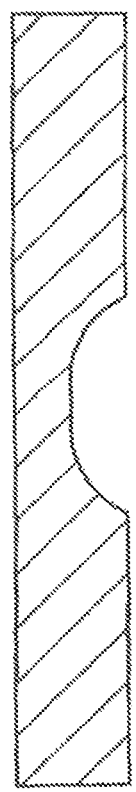

Constants were the minimum and maximum wall thicknesses and total height of the model. A parametric study was conducted with every combination of these variables (i.e. 12 total models) to show how these geometric changes affected plasticity. These combinations were labeled by their length (L0, L1, L2, L3) followed by their radius (R2, R4, R8), e.g. L3R8. The two extreme cases of these models (L0R2 and L3R8) are illustrated in FIGS. 10A and 10B for clarity. Detailed information on how the 2D-axisymmetric-with-twist model was created is set forth below in Appendix A.

By lengthening the flattened bottom section of the groove in a tube section and reducing the stress concentrations from the fillet radii in a 2D axisymmetric model, the percent of work that went into plastic energy dissipation was increased by 36%. In addition, the radians that the structure rotated before failure was shown to increase by 74%, along with the area experiencing plastic yielding. All these results were consistent, showing that the plasticity of a structure is dependent on the specific geometry surrounding the failure region.

In all cases the maximum torque required for the structure to experience torsional failure was almost identical. This result indicates that the failure strength of a tube under torsion is primarily a function of the failure region's mean thickness, which remained constant, and therefore was not affected by surrounding geometries.

Figure 11A:
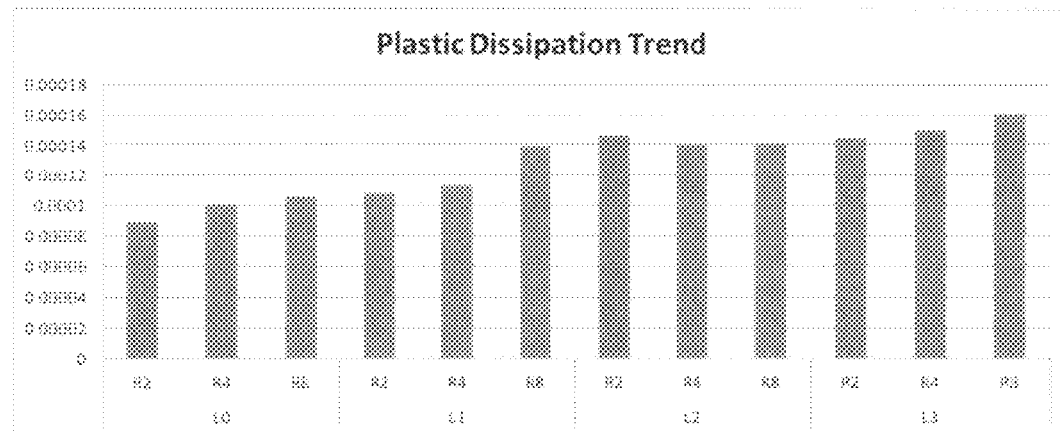
FIGS. 11A-C reports pivot graph results of the parametric Abaqus model testing showing (from top to bottom) Abaqus variables ALLPD (11A), ALLSE (11B), ALLWK (11C).

The general trend of geometry to plastic dissipation can best be seen by the pivot table graph in FIG. 11A. It also shows the two geometries that have the lowest and highest values of plastic dissipation. As expected, due to what is known about stress risers, the smaller groove with the smallest radius has the lowest plastic dissipation and the widest groove with the largest radius has the greatest plastic dissipation. The relatively sharp groove in L0R2 has only a small area of influence, while the widest groove of L3R8 spans, and therefore affects, much more material. Since more material is influenced by the stress riders of L3R8, there will be more elements experiencing plastic deformation.

Figure 12A:
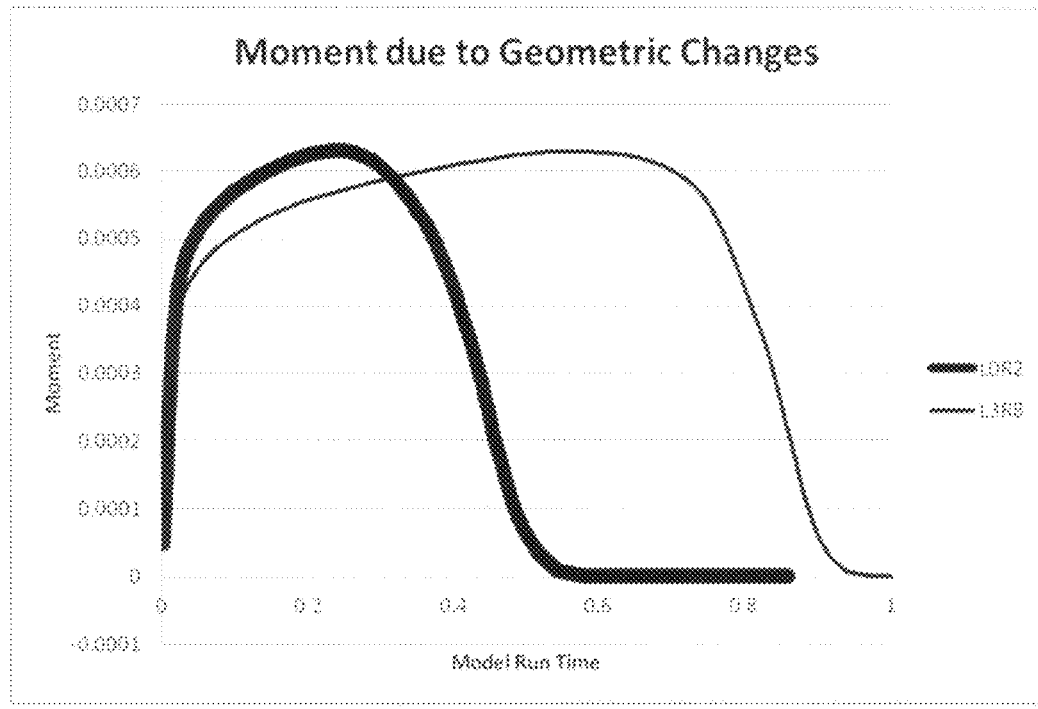
FIGS. 12A and 12B provide graphs comparing the output of axisymetric-with-twist computer modeling trials showing: (A) The maximum moment remains relatively constant while increasing in duration; and (B) The plastic dissipation of energy and total displacement (strain) increases significantly.
Figure 12B:
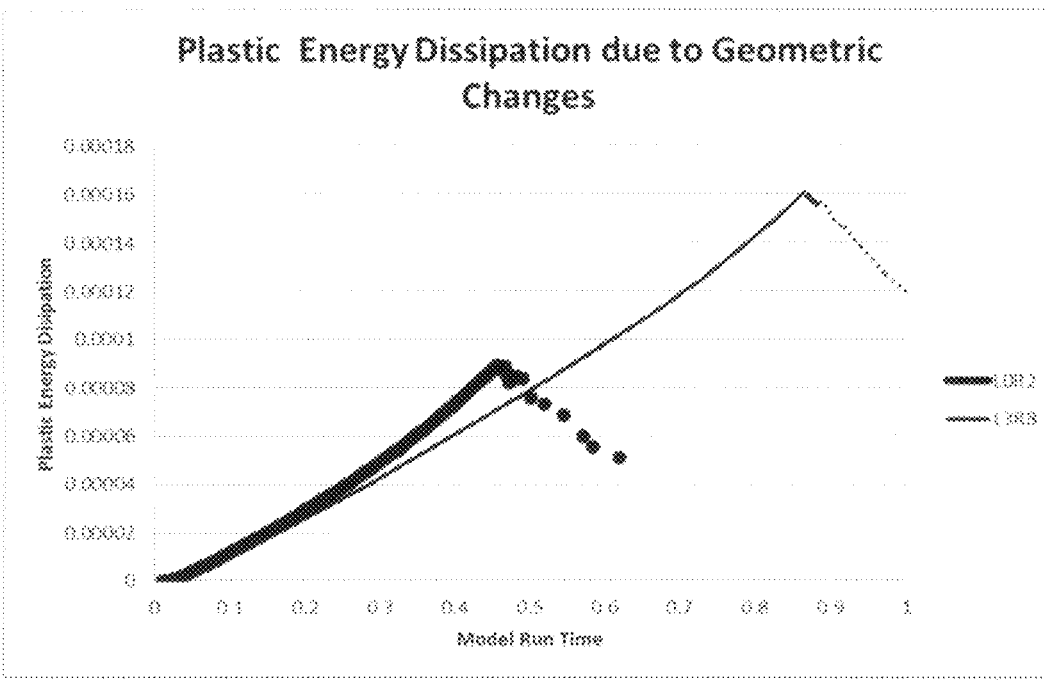
Figure 13A:
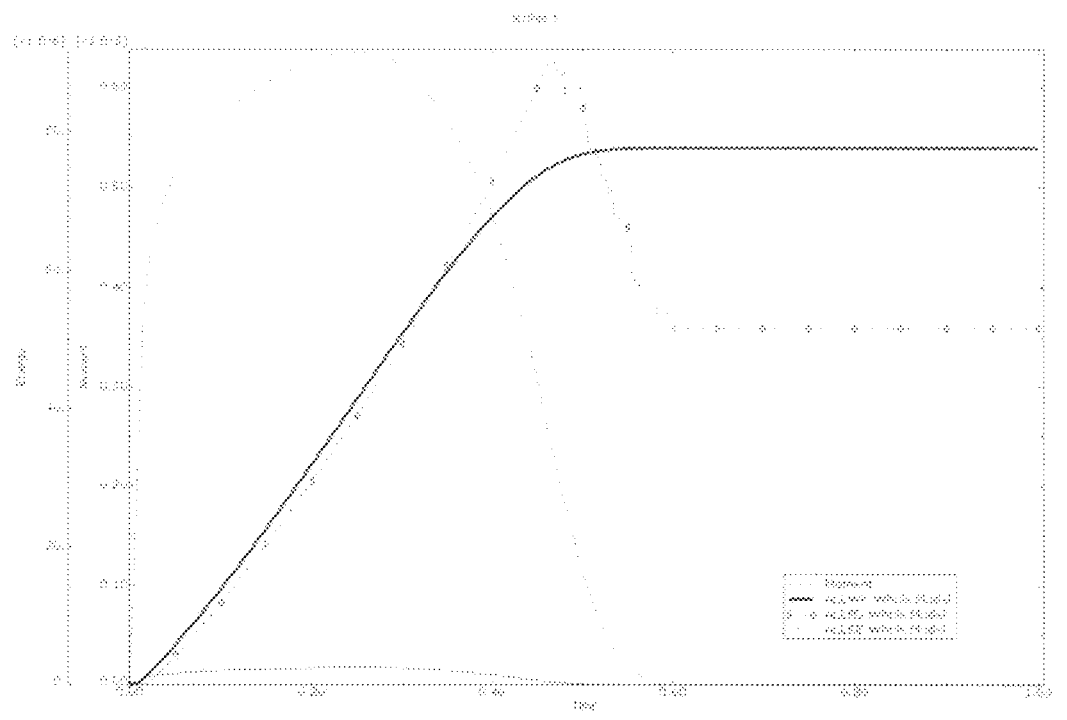
FIGS. 13A and 13B provide graphical results of the energy and moment values for the plastic dissipation shown in FIGS. 12A and 12B respectively. The thick line shows the point where first yield occurs, the circle at the peak shows where the first element is deleted, and the second circle shows where the final element is deleted.
Figure 13B:
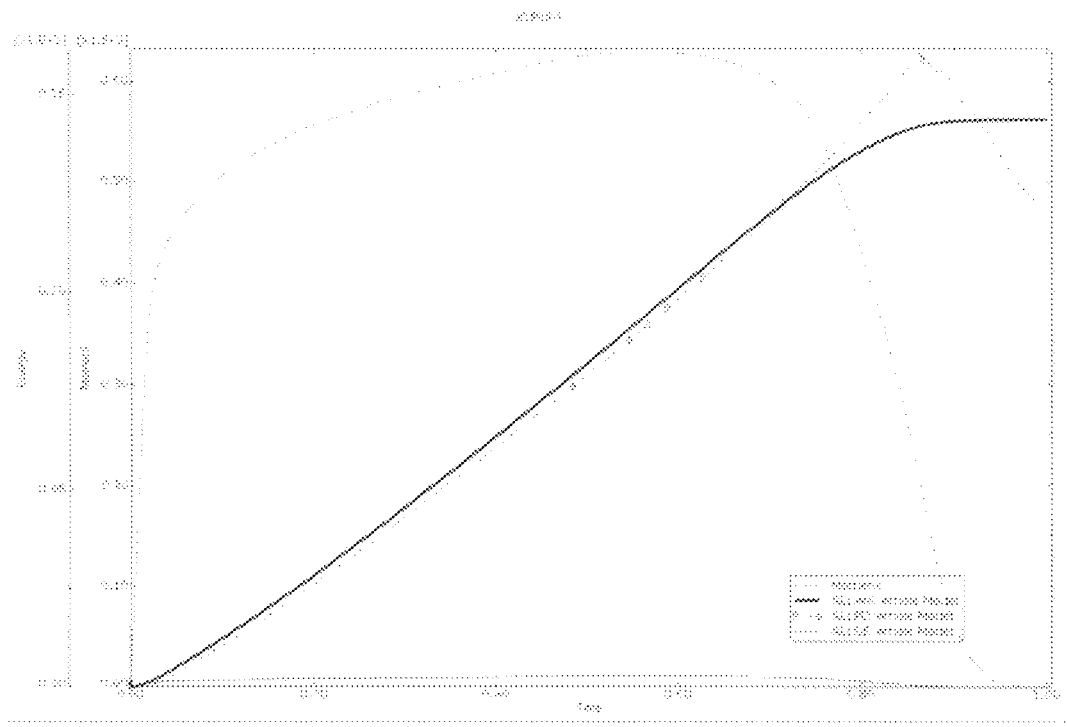

Despite the change in stress concentrations, the maximum moment required to shear each cross section experienced negligible variation (FIG. 12A. Therefore, since the minimum cross section did not change, this moment remains primarily a function of the thinnest cross section of the groove as predicted by the equations above in Example 1. However, the increased amount of displacement over which the moment must be applied causes the external work done on the structure to increase, since work is force times displacement. FIG. 12A illustrates the relative shapes of the moment curves for L0R2 and L3R8. Additionally, whereas FIG. 11A shows the relative maximums of the plastic dissipation ("ALLPD"), FIG. 12B shows the curve profile for the trials for L0R2 and L3R8. The decreasing plastic dissipation energy ("ALLPD") term in FIG. 11A is believed to be an inaccurate artifact due to element deletion. When the elements were deleted after they had reached the complete failure criteria defined by the material model, the energy terms associated with those elements are also deleted. This also shows that the deformation occurred at a slower rate and over a longer time when comparing the wider L3R8 groove to the narrow L0R2 groove, which is useful because more elongation means more plastic dissipation as discussed above. The displacement at which the structure completely fails for the L0R2 model was 0.54 of the rotation cycle, and the displacement at which the structure completely fails for the L3R8 model was 0.94 of the rotation cycle. This is a 74% increase in rotation before failure. The researchers consider this entire increase to be due to plastic strain, since only 3.09E−7 of the rotation cycle is completely elastic for the L0R2 model and 0.0142 is elastic for L3R8. Using the geometric extremes, the behavior of the structure in relation to the curve profiles is shown in FIGS. 13A-B. It should be noted that complete failure was defined by the researchers to be the moment when the last element was deleted, and this point is not the same moment when the ALLPD curve becomes level.

Figure 11B:
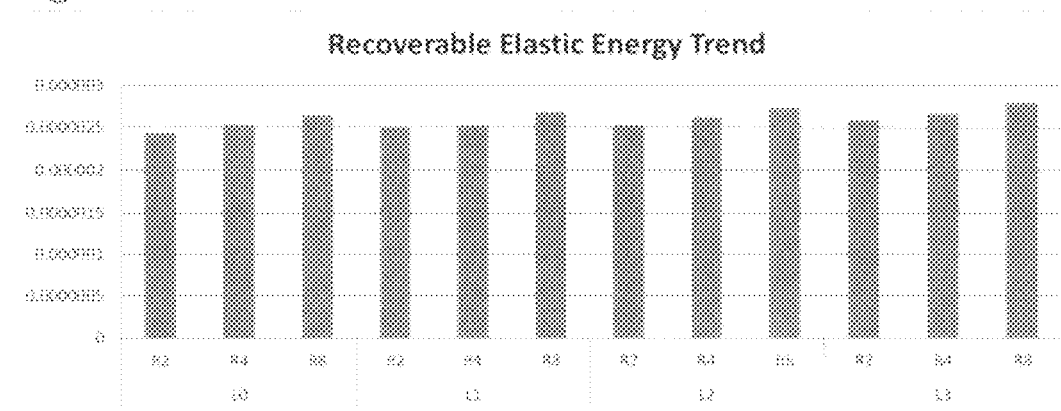
Figure 11C:
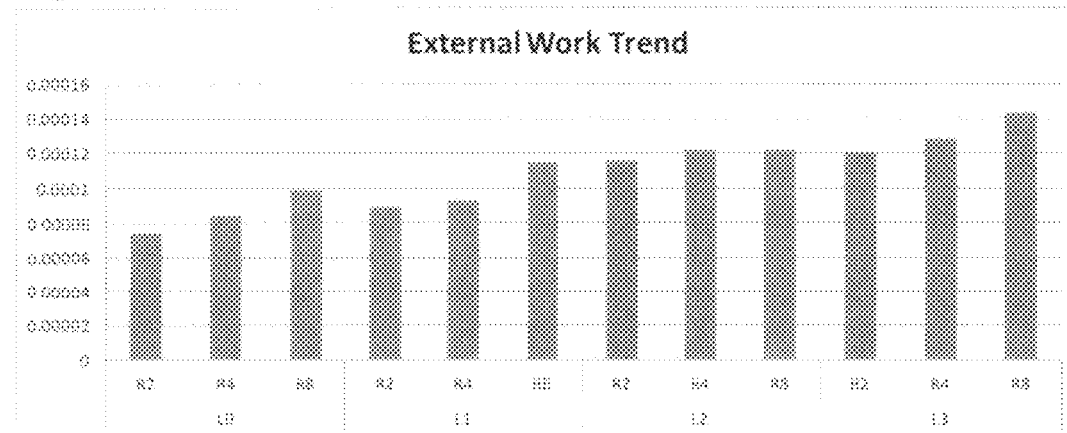

Although the recoverable elastic energy is slightly higher for L3R8 than for L0R2 (FIG. 11B), this increase is negligible considering the overall magnitude of the work done as shown by the output graphs of L0R2 and L3R8 in FIGS. 13A, 13B. As discussed above, this is the reason why the ratio of recoverable elastic strain to plastic energy dissipation was used. Numerically, the ALLSE/ALLPD ratio for the smallest groove (L0R2) was 0.0274, and the same ratio for the largest groove (L3R8) was 0.0174. This is over a 36% decrease in the ratio, showing that the geometric structure influences the plastic behavior of a material. A numerical summary of results for L0R1 and L3R8 is found in Table 3.

TABLE 3

Comparison of the two geometric extremes L0R2 and L3R8

|  | Maximum Elastic energy (ALLSE) | Maximum Plastic dissipation energy (ALLPD) | ALLSE/ ALLPD | Total work done (ALLWK) | Rotation before complete shear failure | Maximum moment for shear failure |
|---|---|---|---|---|---|---|
| L0R2 | 2.442E−06 | 8.902E−05 | .0274 | 7.430E−05 | 9.28° | 6.307E−04 |
| L3R8 | 2.796E−06 | 16.073E−05 | .0174 | 14.352E−05 | 16.16° | 6.293E−04 |
|  |  |  | 36% Decrease |  | 74% Increase | Approximately the same |

In summary, geometric changes to the groove profile around the outer circumference of the tube caused plasticity to increase, as indicated by a decrease in the ratio of elastic energy to plastic dissipation energy and an increase in radians revolved before complete shear failure. Through all geometries, the tube was a constant material (Al-5083-H116) and the maximum moment before failure remained approximately constant.

It is thus evident that the reduced shock breakaway set screw constructed as described herein substantially improves the art. Only particular embodiment(s) have been presented and described in detail, and the invention should not be limited by the drawings or the description provided. For an appreciation of the true scope and breadth of the invention, reference should be made only to the claims that follow.

APPENDIX A

Abaqus (Version 6.10-2) Steps Used to Build the 2D Axisymmetric Model with Twist Notes:
2D axi-symmetric CGAX3 element gives additional twist angle degree of freedom
Disadvantage of axisymmetric is that one cannot use explicit methods
Units of values must be kept consistent by the user
PART MODULE: . . . (from pull-down window just above view-port . . . ) Select "Module: Part"
1) CREATING THE PART . . . (from top menu . . . ) "Part", "Create . . . ",
   a) name the part "tube" on the text input box, select "Axisymmetric", select "Deformable", select "Shell", check "Include twist" (creates a generalized axisymmetric model that allows rotational movements and force calculations), specify "Approximate size" to at least twice as big as the greatest cross section length or the radius, whichever is greatest (For this thesis: 0.012), click "Continue"
   b) Draw desired cross-section with a defined radius. For L0R2 groove in this thesis:
      i) 0.00265 radius (length from center line to left-most straight edge of tube wall), 0.0058 tube height (continuous vertical dimensioned length on the left side, two non-dimensioned vertical lengths on the right where one extends from the base and one extends from the top, but neither touch one another), 0.0008 regular wall thickness on the upper and lower horizontal boundaries of the tube cross section
      ii) Define the groove by:
         (1) Draw a short straight edge extending from the ends of the nearby right vertical lines toward the left side, constrain these lines as horizontal
         (2) Draw a semi-circle (defined by two points) between the ends of the two new straight lines, defining the semi-circle radius (L0R2 groove is 0.0002), create a "tangent" constraint between the semi-circle and the two new horizontal lines
         (3) Draw an "Isolated Point" midway on the circumference of the semi-circle location marker will indicate when this point is being selected by turning from a cross to a filled-in circle)
         (4) Define the length between this new point and the left edge (For this thesis: 0.0004)
      iii) Confirm the sketch created is a closed structure, otherwise it will be invalid
   c) Hit "Esc" on keyboard
   d) Click "Done" just below the view-port
2) PARTITIONING THE PART . . . (from top menu . . . ) "Tools", "Partition . . . ", select "Face", select "Sketch"
   a) (from top menu . . . ) "Add", "Line", "Rectangle"
   b) Click the left-top corner of the tube-wall to start the first box and click somewhere just above the groove on the right side of the tube-wall
   c) Click the left-bottom corner of the tube-wall to start the second box and click somewhere just below the groove on the right side of the tube-wall
   d) (from top menu . . . ) "Add", "Dimension", define the length slightly away from the start of the groove on both sides such that the region of interest does not extend into either box (For this thesis, the plastic deformation will not extend into either box if both lengths are 0.0002)
   e) Hit "Esc" on keyboard
   f) Click "Done" just below the view-port PROPERTY MODULE: . . . (from pull-down window just above view-port . . . ) Select "Module: Property"
3) DEFINING MATERIAL . . . (from top menu . . . ) "Material", "Create . . . " (see APPENDIX B herein for the AL5083-H116 values)
   a) Name the material as desired (For this thesis: "Al5083")
   b) General, Density
   c) Mechanical, Elasticity, Elastic (E, Poisson's ratio)
   d) Mechanical, Plasticity, Plastic (tabular input of "Yield Stress" and "Plastic Strain")
   e) Mechanical, Damage for Ductile Metals, Ductile Damage
      i) Tabular input of "Fracture Strain" and "Stress Triaxiality" (zero for strain rate)
      ii) Suboptions, Damage Evolution, "Type: Displacement", "Softening:Linear", "Degradation:Maximum", "Displacement at Failure" should be 25% or less of your element seeded length (for this thesis: 0.25* seeded length of 4E−005=1E−005). This value is the amount of elongation an edge will have after the failure criteria is met, and is similar to defining the amount of strain occurring in the necking region of an engineering stress-strain curve
4) CREATE SECTION
   a) (from top menu . . . ) "Section", "Create . . . "
   b) Name the section as desired (For this thesis: "tube_sec"), select "Solid", select "Homogeneous"
   c) Click "Continue"
   d) Select the proper material (For this thesis: "Al5083")
   e) Check "Plane stress/strain thickness:" and leave value as "1"
   f) Click "OK"
5) ASSIGN SECTION
   a) (from top menu . . . ) "Assign", "Section"
   b) Select the regions of the part from the viewport that must be associated with the section just created (For this thesis, there are 3 regions)
   c) Hit "Enter" on keyboard
   d) Select the desired section (For this thesis: "tube_sec")
   e) In the "Thickness" section of the window, leave the "Assignment" selection as "From section"
   f) Click "OK"
   g) Hit "Esc" on keyboard
MESH MODULE: . . . (from pull-down window just above view-port . . . ) Select "Module:Mesh"
6) MESHING THE PART
   a) (from top menu . . . ) "Seed", "Edges . . . "
      i) HOLD THE "SHIFT" KEY and select all edges bordering the region of interest, including the nearby partition borders (For L0R2 groove, this should be 7 straight edges and one semi-circular edge)
      ii) Hit "Enter" on keyboard
      iii) Keep defaults and define "Approximate element size:" under "Sizing Controls" (For this thesis: 4E−005)
      iv) Click "OK"
      v) HOLD THE "SHIFT" KEY and select the remaining faces (For this thesis, there should be 6 straight edges)
      vi) Hit "Enter" on keyboard
      vii) Keep defaults and define "Approximate element size:" under "Sizing Controls" (For this thesis: 0.0001)

viii) Click "OK"
ix) Hit "Esc" on keyboard
b) (from top menu . . . ) "Mesh", "Controls . . . "
  i) HOLD THE "SHIFT" KEY and select all part regions (For this thesis, there are 3 regions)
  ii) Hit "Enter" on keyboard
  iii) Select "Tri", leave default technique as "Free"
  iv) Click "OK"
c) (from top menu . . . ) "Mesh", "Part . . . ", Hit "Enter" on keyboard
d) If the mesh does not exactly match up to the seeded edges and this condition is important to the model (ex. Mesh convergence analysis), then repeat all steps in 6-b EXCEPT un-check the "Use mapped meshing where appropriate" under the "Algorithm" section in the pop-up-window.

ASSEMBLY MODULE: . . . (from pull-down window just above view-port . . . ) Select "Module:Assembly"

7) CREATE ASSEMBLY
  a) (from top menu . . . ) "Instance", "Create . . . "
  b) Select desired part(s) (For this thesis: just "tube"), click "OK" (will automatically assume assigned mesh)

8) CREATE NODE SETS
  a) Line up the viewport to the Y/X-plane
    i) (from top menu . . . ) "View", "Toolbars", "Views" must be checked
    ii) Look for the icon in the upper toolbar that has an up-ward and a right-ward facing arrow labeled "Y" and "X", respectively
    iii) Click this icon
  b) Create the boundary set . . .
    i) (from top menu . . . ) "Tools", "Set", "Create . . . "
    ii) Name it "BOUNDARY", select "Node", click "Continue"
    iii) Click & drag to box/select desired nodes (For this thesis: only the nodes located on the bottom edge of the tube). HOLD THE "SHIFT" KEY and select addition nodes if desired.
    iv) Hit "Enter" on keyboard
  c) Create the loading set . . .
    i) (from top menu . . . ) "Tools", "Set", "Create . . . "
    ii) Name it "LOAD", select "Node", click "Continue"
    iii) Click & drag to box/select desired nodes (For this thesis: only the nodes located on the top edge of the tube). HOLD THE "SHIFT" KEY and select addition nodes if desired.
    iv) Hit "Enter" on keyboard STEP MODULE: . . . (from pull-down window just above view-port . . . ) Select "Module:Step"

9) CREATE LOADING STEP
  a) (from top menu . . . ) "Step", "Create . . . "
  b) Leave name as "Step-1", leave defaults (i.e. "General" & "Static, General")
  c) Click "Continue"
  d) On the initial "Basic" tab, select "On" for Nlgeom (so large displacements can be considered)
  e) Select the "Incrementation" tab
    i) Leave default "Type" as "Automatic"
    ii) Increase maximum number of increments so this does not limit the calculations (For this thesis: 10,000)
    iii) Leave everything else as default to start with. If later runs produce errors, then "Increment size:" values may need adjusted. (For this thesis: "Initial" was adjusted to 0.001)
    iv) Click "OK"

10) MODIFY OUTPUT VARIABLES TRACKED
  a) (from top menu . . . ) "Output", "Field Output Requests", "Edit", "F-Output-1"
  b) Leave already selected values alone
  c) Expand "Forces/Reactions", select RM "Reaction moments"
  d) Expand "Failure/Fracture", select DMICRT "Damage initiation criteria"
  e) Expand "State/Field/User/Time", select STATUS "Status (some failure and plasticity models; VUMAT)"

LOAD MODULE: . . . (from pull-down window just above view-port . . . ) Select "Module:Load"

11) CREATE FIXED BOUNDARY CONDITIONS
  a) (from top menu . . . ) "BC", "Create . . . "
  b) Name as desired, change "Step:" to "Initial"
  c) "Category" is "Mechanical", select "Displacement/Rotation"
  d) Click "Continue"
  e) Click "Sets . . . " (at the bottom right of the view-port)
  f) Select the "BOUNDARY" set, click "Continue"
  g) Check U1, U2, UR2, and UR3, click "OK"

12) CREATE ROTATING BOUNDARY CONDITIONS
  a) Since the torsion of the tube top is displacement controlled (as opposed to force controlled), it must be defined as a boundary condition: (from top menu . . . ) "BC", "Create . . . "
  b) Name as desired, change "Step:" to "Step-1"
  c) "Category" is "Mechanical", select "Displacement/Rotation"
  d) Click "Continue"
  e) Click "Sets . . . " (at the bottom right of the view-port)
  f) Select the "LOAD" set, click "Continue"
  g) Check UR2, set value to radians of rotation for the loaded set (For this thesis: 0.3), click "OK"

JOB MODULE: . . . (from pull-down window just above view-port . . . ) Select "Module:Job"

13) CREATE JOB
  a) (from top menu . . . ) "Job", "Create . . . "
  b) Name as something OTHER than "Job-1" (this name causes an error for some reason), leave defaults, click "Continue"
  c) Leave defaults, click "OK"

14) RUN JOB: (from top menu . . . ) "Job", "Submit", select the desire job

15) VIEW RESULTS: (from top menu . . . ) "Job", "Results", select the desire job

APPENDIX B

| AI5083-H116 Parameters Used in the Model | | | | |
|---|---|---|---|---|
| Density (lbf s²/in⁴) | Young's Modulus (psi) | Poisson's Ratio | Displacement at Failure | Seed size in shear region |
| 0.00025 | 9926807.662 | 0.3 | 1E-005 | 4E-005 |
| Fracture Strain | | | Stress Triaxiality | |
| 0.3 | | | 0 | |
| 0.2 | | | 0.33 | |
| 0.1 | | | 0.8 | |
| 0.1 | | | 1 | |
| Yield Stress (psi) | | | Plastic Strain | |
| 30000.0 | | | 0.000000000 | |
| 31069.9 | | | 0.000870102 | |
| 31948.7 | | | 0.001781570 | |
| 32685.2 | | | 0.002707380 | |
| 33609.7 | | | 0.004114250 | |

APPENDIX B-continued

| Al5083-H116 Parameters Used in the Model | |
|---|---|
| 34571.9 | 0.005917320 |
| 35825.8 | 0.008891000 |
| 37076.5 | 0.012713700 |
| 38087.2 | 0.016560700 |
| 38939.1 | 0.020423600 |
| 39677.6 | 0.024297900 |
| 40330.9 | 0.028180900 |
| 40917.5 | 0.032070500 |
| 41450.6 | 0.035965500 |
| 41939.6 | 0.039865000 |
| 42529.3 | 0.045015700 |
| 43402.1 | 0.053627800 |
| 44434.4 | 0.065523800 |
| 45526.0 | 0.080413800 |
| 46460.3 | 0.095319700 |
| 47536.8 | 0.115321000 |
| 48875.8 | 0.145076000 |
| 50665.4 | 0.194896000 |
| 53299.4 | 0.294631000 |
| 55251.0 | 0.394434000 |
| 56813.8 | 0.494277000 |
| 58123.4 | 0.594145000 |
| 59254.3 | 0.694031000 |
| 60251.6 | 0.793930000 |
| 61145.2 | 0.893840000 |
| 61955.8 | 0.993759000 |

What is claimed is:

1. A reduced shock breakaway set screw for use with a surgical construct comprising a threaded lower portion and an upper head portion separated by a substantially annular groove having an upper radius, a lower radius, and a substantially flattened portion separating said upper radius and said lower radius; and an internal opening extending from said upper head portion into said threaded lower portion; a plurality of ridges running across said substantially annular groove and a plurality of apertures separate and apart from said plurality of ridges and extending between said internal opening and said substantially annular groove.

2. The reduced shock breakaway set screw of claim 1 wherein said reduced shock breakaway set screw is made of metal.

3. The reduced shock breakaway set screw of claim 2 wherein said reduced shock breakaway set screw is made from a metal selected from the group consisting of titanium and stainless steel.

4. The reduced shock breakaway set screw of claim 3 wherein the metal is titanium.

5. The reduced shock breakaway set screw of claim 1 wherein said internal opening extends from said upper head portion to the top of said threaded lower portion.

6. The reduced shock breakaway set screw of claim 5 wherein said threaded lower portion further comprises a recess sized to mate with a tool for removing screws.

7. The reduced shock breakaway set screw of claim 1 wherein said upper radius is from 1/64 inches to 1/4 inches and said lower radius is from 1/64 inches to 1/4 inches.

8. The reduced shock breakaway set screw of claim 1 wherein said substantially flattened portion has a length of from more than 0 inches to 1/8 inch or less.

9. A reduced shock breakaway set screw for use with a surgical construct comprising a threaded lower portion and an upper head portion separated by a substantially annular groove; an internal opening extending from said upper head portion into said threaded lower portion; a plurality of ridges running across said substantially annular groove; and a plurality of apertures separate and apart from said plurality of ridges and extending between said internal opening and said substantially annular groove.

10. The reduced shock breakaway set screw of claim 9 wherein said reduced shock breakaway set screw is made from a metal selected from the group consisting of titanium and stainless steel.

11. The reduced shock breakaway set screw of claim 9 wherein said internal opening extends from said upper head portion to the top of said threaded lower portion.

12. The reduced shock breakaway set screw of claim 9 wherein said threaded lower portion further comprises a recess sized to mate with a tool for removing screws.

* * * * *